(12) United States Patent
Andersson et al.

(10) Patent No.: US 9,157,888 B2
(45) Date of Patent: Oct. 13, 2015

(54) FIELD EFFECT TRANSISTOR FOR CHEMICAL SENSING USING GRAPHENE, CHEMICAL SENSOR USING THE TRANSISTOR AND METHOD FOR PRODUCING THE TRANSISTOR

(75) Inventors: Mike Andersson, Linkoping (SE); Lars Hultman, Linkoping (SE); Anita Lloyd Spetz, Linkoping (SE); Ruth Pearce, London (GB); Rositsa Yakimova, Linkoping (SE)

(73) Assignee: GRAPHENSIC AB, Linkoping (SE)

( * ) Notice: Subject to any disclaimer, the term of this patent is extended or adjusted under 35 U.S.C. 154(b) by 0 days.

(21) Appl. No.: 14/115,818

(22) PCT Filed: May 5, 2011

(86) PCT No.: PCT/SE2011/050565
§ 371 (c)(1),
(2), (4) Date: Nov. 5, 2013

(87) PCT Pub. No.: WO2012/150884
PCT Pub. Date: Nov. 8, 2012

(65) Prior Publication Data
US 2014/0070170 A1    Mar. 13, 2014

(51) Int. Cl.
*H01L 29/06* (2006.01)
*G01N 27/414* (2006.01)

(52) U.S. Cl.
CPC ........ *G01N 27/4146* (2013.01); *G01N 27/4141* (2013.01); *H01L 29/0673* (2013.01)

(58) Field of Classification Search
CPC ............... H01L 29/1606; H01L 29/78696; H01L 29/0673; G01N 27/414; G01N 27/4143
USPC .......................................................... 257/29
See application file for complete search history.

(56) References Cited

U.S. PATENT DOCUMENTS

| 4,058,368 A | 11/1977 | Svensson et al. |
| 4,411,741 A | 10/1983 | Janata |

(Continued)

FOREIGN PATENT DOCUMENTS

| EP | 1666873 A1 | 6/2006 |
| WO | 2012036608 A1 | 3/2012 |

OTHER PUBLICATIONS

Lundström, I., et al., A hydrogen-sensitive MOS field-effect transistor, Applied Physics Letters, 1975, pp. 55-57, vol. 26.

(Continued)

*Primary Examiner* — Lex Malsawma
*Assistant Examiner* — Laura Dykes
(74) *Attorney, Agent, or Firm* — Hultquist, PLLC; Steven J. Hultquist (57) ABSTRACT

A field effect transistor (20) for chemical sensing, comprising an electrically conducting and chemically sensitive channel (2) extending between drain (5) and source (6) electrodes. A gate electrode (7) is separated from the channel (2) by a gap (10) through which a chemical to be sensed can reach the channel (2) which comprises a continuous monocrystalline graphene layer (2a) arranged on an electrically insulating graphene layer substrate (1). The graphene layer (2a) extends between and is electrically connected to the source electrode (5) and the drain electrode (6). The substrate supports the graphene layer, allowing it to stay 2-dimensional and continuous, and enables it to be provided on a well defined surface, and be produced and added to the transistor as a separate part. This is beneficial for reproducibility and reduces the risk of damage to the graphene layer during production and after. Low detection limits with low variability between individual transistors are also enabled. There is also provided a chemical sensor (30) using the transistor (20) and a method for providing the transistor (20).

23 Claims, 2 Drawing Sheets

(56) References Cited

U.S. PATENT DOCUMENTS

| | | | |
|---|---|---|---|
| 4,514,263 | A | 4/1985 | Janata |
| 2007/0132043 | A1 | 6/2007 | Bradley et al. |
| 2011/0057168 | A1 | 3/2011 | Kobayashi |
| 2012/0058350 | A1* | 3/2012 | Long et al. .............. 428/446 |

OTHER PUBLICATIONS

Novoselov, K.S., et al., Electric Field Effect in Atomically Thin Carbon Films, Science, Oct. 22, 2004, pp. 666-669, vol. 306.
Schedin, F., et al., Detection of individual gas molecules adsorbed on graphene, Natural Materials, Jul. 29, 2007, pp. 652-655, vol. 6.
Cheng, Z., et al., Suspended Graphene Sensors with Improved Signal and Reduced Noise, Nano Letters, 2010, pp. 1864-1868, vol. 10.
Lu, G., et al., Toward Practical Gas Sensing with Highly Reduced Graphene Oxide: A New Signal Processing Method to Circumvent Run-to-Run and Device-to-Device Variations, ACS Nano, 2011.
Yakimova, R., et al., Analysis of the Formation Conditions for Large Area Epitaxial Graphene on SiC Substrates, Materials Science Forum, 2010, pp. 565-568, vols. 645-648.
Varchon, F., et al., Electronic Structure of Epitaxial Graphene Layers on SiC: Effect of the Substrate, Physical Review Letters, 2007, pp. 126805-1-126805-4, vol. 99.
Zhou, S., et al., Substrate-induced bandgap opening in epitaxial graphene, Nature Materials, Oct. 2007, pp. 770-775, vol. 6.
Star, A., et al., Gas Sensor Array Based on Metal-Decorated Carbon Nanotubes, Journal of Chemical Physics B, 2006, pp. 21014-21020, vol. 110, No. 42.
Qui, P., et al., Toward Large Arrays of Multiplex Functionalized Carbon Nanotube Sensors for Highly Sensitive and Selective Molecular Detection, Nano Letters, 2003, pp. 347-351 vol. 3, No. 3.
Sensic AB et al., International Application No. PCT/SE2011/050565, International Search Report, Jan. 12, 2012.
Sensic AB et al., International Application No. PCT/SE2011/050565, Written Opinion, Jan. 12, 2013.
Sensic AB et al., International Application No. PCT/SE2011/050565, Written Opinion of the International Preliminary Examining Authority, May 6, 2013.
Sensic AB et al., International Application No. PCT/SE2011/050565, International Preliminary Report on Patentability, Aug. 19, 2013.
Sudibya, H.G., et al., Electrical Detection of Metal Ions Using Field-Effect Transistors Based on Micropatterned Reduced Graphene Oxide Films, American Chemical Society Nano, 2011, pp. 1990-1994, vol. 5, No. 3.
Chen, F., et al., Ionic Screening of Charged-Impurity Scattering in Graphene, 2009, pp. 1621-1625, vol. 9, No. 4.
Dan, Y., et al., Intrinsic Response of Graphene Vapor Sensors, Nano Letters, 2009, pp. 1472-1475, vol. 9, No. 4.
Li, J. et al., Nafion-graphene nanocomposite film as enhanced sensing platform for ultrasensitive determination of cadmium, Electrochemistry Communications, 2009, pp. 1085-1088, vol. 11.
Chen, W., et al., Atomic structure of the 6H-SiC(0001) nanomesh, Surface Science, 2005, pp. 176-186, vol. 596.
Ang, P.K., et al., Solution-Gated Epitaxial Graphene as pH Sensor, Journal of the American Chemical Society, 2008, pp. 14392-14393, vol. 130, No. 44.
Gong, J., et al., Monodispersed Au nanoparticles decorated graphene as an enhanced sensing platform for ultrasensitive stripping voltammetric detection of mercury (II), Sensors and Actuators B: Chemical, 2010, pp. 491-497, vol. 150.
Ristein, J., et al., Characteristics of solution gated field effect transistors on the basis of epitaxial graphene on silicon carbide, 2010, Journal of Physics D: Applied Physics, pp. 1-9, vol. 43.
Sensic AB, European Application No. 11864886.4, Extended European Search Report, Sep. 17, 2014.

* cited by examiner

FIELD EFFECT TRANSISTOR FOR CHEMICAL SENSING USING GRAPHENE, CHEMICAL SENSOR USING THE TRANSISTOR AND METHOD FOR PRODUCING THE TRANSISTOR

TECHNICAL FIELD

The present disclosure relates generally to chemical sensing using field effect transistors and more particularly to chemical sensing using field effect transistors with a chemically sensitive channel involving graphene.

TECHNICAL BACKGROUND

Chemical sensing using field effect transistors (FETs), for example, a FET capable of detecting gas as described in the 1975 article I. Lundström, "*A Hydrogen-Sensitive MOS Field-Effect Transistor*" *Applied Physics Letters* 26, 55-57 and in U.S. Pat. No. 4,058,368 awarded to Svensson et. al. In the aforementioned article the transistor device has a palladium gate that is catalytically active with hydrogen dissociatively adsorbing and atomic hydrogen then absorbing into the palladium gate.

Chemically sensitive FETs with an air gap between the channel and the gate have been described in e.g. Janata's 1985 U.S. Pat. Nos. 4,514,263 and 4,411,741 which describe a chemically sensitive field effect transistor with an air gap for measuring components in either gases or liquids. These FETs are similar to the Lundström MOSFET in that they both include a doped semiconductor substrate which acts as a channel and a pair of doped regions forming source and drain electrodes, however in Janata's device the metal gate is suspended above the semiconductor substrate, defining an air gap. A voltage is applied to the gate and when gases or liquids with a dipole moment are introduced into the air gap, they are attracted to the charged gate or to the semiconductor surface.

When chemically sensitive FETs are used in chemical sensing applications, that is, when such a FET is used in/as a sensor, the sensor further comprises means for electrically controlling and/or biasing the FET for sensing so that detection of the chemical will manifest as or in an electrical signal, which thus becomes a chemical indicative electrical signal. By predetermining the relation between the sensed chemical, e.g the concentration thereof, and the resulting chemical indicative electrical signal, the electrical signal can be used solely, not only to detect presence or not of the chemical, but also to determine the amount, typically the concentration, of the chemical.

Following the isolation of graphene in 2004 by K. S. Novoselov et al, "*Electric Field Effect in Atomically Thin Carbon Films*" Science, 306, 5696, 666-669, its use in various application areas has been investigated, including for chemical sensing applications. Lower detection limits have become possible, in part due to the low noise of graphene transistors and also due to the high surface area and the large field effect in graphene which enables large shifts in the Fermi level by applying a gate voltage, thus tuning the electronic properties for sensor applications.

Parts-per-billion detection was demonstrated in the 2007 article Schedin et. al., "*Detection of individual gas molecules adsorbed on graphene*", *Nature Materials*, 6, 9, 652-655, and showed stepped noise indicating individual molecular adsorption and desorption events. In the aforementioned article, the graphene was in the form of small cleaved flakes.

The detailed mechanism behind the detection in graphene sensors is still a hotly debated topic, however, there is no doubt that graphene can be used in chemical sensing applications and that it enables lower detection limits than in conventional chemical sensing.

In Z. Cheng et. al., *Nano Letters* 10, 1864 (2010), a suspended graphene sensor is disclosed. It comprises a graphene field effect transistor (Gra-FET) fabricated from a mechanically exfoliated graphene supported on a silicon/silicondioxide substrate. Source-drain contacts of Cr/Au is defined by e-beam lithography and subsequent metallization. A polydimethylsiloxane (PDMS) chamber is incorporated over the "Gra-FET" chip to confine an electrolytic solution and a non leak Ag/AgCl reference electrode is used as an electrolyte gate. Etching of the silicon oxide underneath the graphene is carried out in situ to accomplish the suspension and make comparison possible between a situation with and without suspension, showing that suspension improved the sensing properties. However, the sensor is not practical, accomplishing suspension by in situ-etching is cumbersome and is prone to result in differences in the suspension between individual sensors, risk of damage to the graphene layer during the etching and risk of damage to the graphene layer when the substrate has been etched away under it.

A general problem with this device, and often a general problem with many disclosed devices involving graphene at the present date or at present, is that they are mainly designed for experimental purposes and not to be realizable as commercial products for practical use. They therefore, more often than not, have problems in areas such as robustness, reproducibility, individual variability, production yield and cost efficiency. For example, when low detections limits are sought, it does not matter if one individual sensor can be made very sensitive if this is not repeatable so that many sensors with, in principle, equal sensitivity and low detection limit can be manufactured, or, if the sensor, during use or manufacture, is likely to or too easily may have its sensibility negatively affected. Damage to the graphene layer may destroy or at least impair the chemical sensing capabilities. Since the degree and impact of damages typically are, more or less, random in nature, also small damages may contribute to undesirable individual variability among sensors of the same type and construction, which may be a particular problem for sensors with low detection limits, as enabled by graphene. It is therefore desirable to reduce the risk of damage to the graphene layer to the greatest extent possible.

A step toward practical gas sensing involving graphene was taken in the 2011 article G Lu et. al., "*Toward practical gas sensing with highly reduced graphene oxide: A new signal processing method to circumvent run-to-run and device-to-device variations*", *ACS Nano*, in press/published online. The article discusses fabrication and characterization of gas sensors using a back-gated FET platform with chemically reduced graphene oxide as the conducting channel, and signal processing method that addresses device-to-device variations. The gate is a silicon wafer and on top of the gate there is a silicondioxide layer onto which Cr/Au electrodes were fabricated using e-beam lithography. A few drops of reduced graphene oxide suspension were cast onto the fabricated electrodes to accomplish a network of suspended reduced graphene oxide platelets left on the electrodes after solvent evaporation. The network serves as the conducting channel between the drain and source electrodes. However, the presented solution results in considerable differences in sensor response between individual devices with uncertainty of placement and thickness of the reduced graphene oxide platelets. Also, the flexible nature of graphene makes suspension of an entire flake unlikely and thus contribution from the $SiO_2$ substrate highly probable.

SUMMARY OF THE INVENTION

In view of the above, an object of this disclosure is to present a solution overcoming or at least alleviating problems in the prior art, or to at least present an alternative solution. A more specific object is to provide a field effect transistor for chemical sensing with graphene as the chemically sensitive material, thereby enabling low detection limits when the transistor is used as or in a chemical sensor, and, at the same time, enabling improvements in regard to robustness, reproducibility and/or individual variability. The invention is defined by the appended independent claims.

Hence, according to a first aspect there is provided a field effect transistor for chemical sensing, comprising a gate electrode, a drain electrode, a source electrode, and an electrically conducting and chemically sensitive channel extending between and being electrically connected to said drain electrode and source electrode, said gate electrode being arranged at a distance from and opposite to said chemically sensitive channel, so that the gate electrode and the chemically sensitive conducting channel are separated by a gap through which a chemical to be sensed can reach the chemically sensitive channel. The chemically sensitive channel comprises a continuous monocrystalline graphene layer arranged on an electrically insulating graphene layer substrate, the graphene layer extending between, and being electrically connected to, the source electrode and the drain electrode. The chemically sensitive channel and the grapheme layer substrate belong to a first separate part that is mounted to a second separate part comprising at least the gate electrode arranged on an insulating surface of a gate substrate. The substrate enables the graphene layer to be provided on a well defined surface and be produced and added to the transistor as a separate part. The substrate also supports the graphene layer and allows it to stay 2-dimensional, continuous and to remain in an intended position. This increases reproducibility and reduces the risk of damage to the graphene layer during production and after. In combination with the monocrystalline continuous graphene layer as such, this also enables low detection limits with low variability between individual transistors.

The graphene layer may have a uniform thickness, preferably a predetermined thickness of one or more monolayers of graphene. As the thickness effects electrical properties, e.g. band gap, carrier concentration etc., a uniform and preferably predetermined thickness provides control of the sensing properties and enables the formation of reproducible devices with low variability between individual sensors.

The graphene layer may be an epitaxial layer and the graphene layer substrate may be the substrate on which the graphene layer was epitaxially grown. By letting the graphene layer remain on the substrate of growth, it is not necessary to handle typically nano-thin graphene layers and structures. Also the risk of damaging the thin graphene layer during manufacturing of the transistor is reduced when the graphene layer can remain on the substrate.

The graphene layer substrate may be a silicon carbide substrate and the graphene layer may have been epitaxially grown on the silicon carbide substrate by sublimation of silicon from the silicon carbide substrate.

The graphene layer may have been surface treated for chemical selectivity so that only selected types of chemicals are detected by the graphene layer and/or so that certain types of chemicals are prevented from reaching the chemically sensitive channel. The surface treatment may comprise deposition of metal particles and/or polymers.

The gap may be arranged directly adjacent to the chemically sensitive channel and in connection with an ambient environment so that the chemical to be sensed can reach the gap from the ambient environment, wherein said ambient environment can be a gaseous ambient environment, such as an air environment, or a liquid ambient environment.

The gate electrode and the chemically sensitive channel may be separated by said gap only.

The gate electrode may be made of metal, such as gold or platinum. The gate electrode may be arranged on an electrically insulating surface of a gate substrate.

The gap may be designed as a flow-through channel, the height of which is defined by the distance between the gate electrode and the chemically sensitive channel.

The flow-through channel may have a closed cross-section. The second part may further comprise the drain electrode and the source electrode arranged on the insulating surface of the gate substrate, and which by the mounting have been brought in physical contact with the first part, thereby establishing the electrical connection between the graphene layer and the source electrode and the drain electrode.

In this way deposition or attachment of the drain electrode and the source electrode separately onto to the graphene layer of the chemically sensitive channel can be avoided. This is advantageous since it is known to be difficult to bond to graphene and processing, e.g. lithography, risks damage to the graphene layer (channel). Instead, when the parts are mounted separately, the electrodes can be pressed against, and in contact with, the chemically sensitive channel, for example by clamping the parts to each other. This also enables the size of the drain electrode and the source electrode to be used to control the height of the gap, which, when the parts are mounted to each other, may be determined by the thicknesses of the drain electrode and the source electrode, which preferably are equal in thickness, minus the thickness of the gate electrode.

According to a second aspect there is provided a chemical sensor comprising the field effect transistor and comprising circuitry arranged to electrically bias the field effect transistor so that a chemical to be sensed which comes in contact with the chemically sensitive channel results in a change of an electrical signal, wherein the change is indicative of the chemical being sensed. By "chemical sensor" it is meant a device with the purpose of sensing a chemical, that is, specifically configured to do this and to provide a response indicative of the chemical being sensed.

In one embodiment the circuitry of the chemical sensor may comprise a current source arranged to flow a constant current between the source electrode and the drain electrode and by comprising a voltage source arranged to supply a constant voltage to the gate electrode, wherein the electrical signal indicative of the sensed chemical is a voltage between the source electrode and the drain electrode.

In another embodiment the circuitry of the chemical sensor may comprise a voltage source arranged to apply a constant voltage between the source electrode and the drain electrode, wherein the electrical signal indicative of the sensed chemical is a gate electrode voltage required to maintain a constant current between the source electrode and the drain electrode.

According to a third aspect there is use of the field effect transistor for chemical sensing. The chemical sensing in the use may comprise guiding a chemical to be sensed from an ambient environment to the gap.

According to a fourth aspect there is provided a method for providing the field effect transistor, wherein the method comprises the steps of: providing a wafer that comprises an epitaxial graphene layer on a silicon carbide wafer substrate; forming the continuous monocrystalline graphene layer of the field effect transistor from the epitaxial graphene layer;

providing the continuous monocrystalline graphene layer arranged on the graphene layer substrate as a first separate part; providing a second separate part comprising the gate electrode arranged on an insulating surface of a gate substrate; and forming the field effect transistor for chemical sensing by mounting the first and second separate parts to each other.

The step of providing the wafer may comprise: providing a silicon carbide wafer substrate; and growing the epitaxial graphene layer on the silicon carbide wafer substrate by sublimation of silicon from the silicon carbide wafer substrate.

The step of forming the continuous monocrystalline graphene layer may comprise: cutting the wafer so that the continuous monocrystalline graphene layer arranged on the graphene layer insulating substrate is formed from a cut piece of the epitaxial graphene layer with underlying part of the silicon carbide wafer substrate.

The second separate part may also comprise the drain electrode and the source electrode arranged on the insulating surface of the gate substrate.

Mounting as separate parts reduces the risk of damaging the graphene layer during manufacturing. Processing, e.g. lithography, which can be detrimental to the graphene layer can thereby be avoided in presence of the graphene layer. Instead processing of the second part can be made in isolation and the mounting of first part with the graphene layer can be performed in a later or last step during manufacturing.

BRIEF DESCRIPTION OF THE DRAWINGS

The above, as well as other aspects, objects and advantages of the present invention, will be better understood through the following illustrative and non-limited detailed description, with reference to the appended schematic drawings.

FIG. 1b schematically shows a bottom view of the field effect transistor for chemical sensing shown in FIG. 1a.

In the drawings the same reference numerals may be used for same, similar or corresponding features, even when the reference numerals refer to features in different embodiments.

DETAILED DESCRIPTION

Figure 1A:
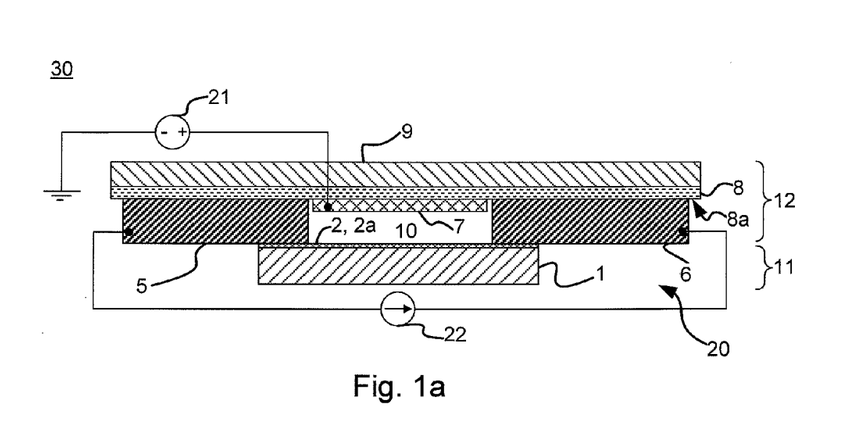
FIG. 1a schematically shows a side view of a field effect transistor for chemical sensing according to a first embodiment and with schematic circuitry biasing the transistor for use as a chemical sensor.
Figure 1B:
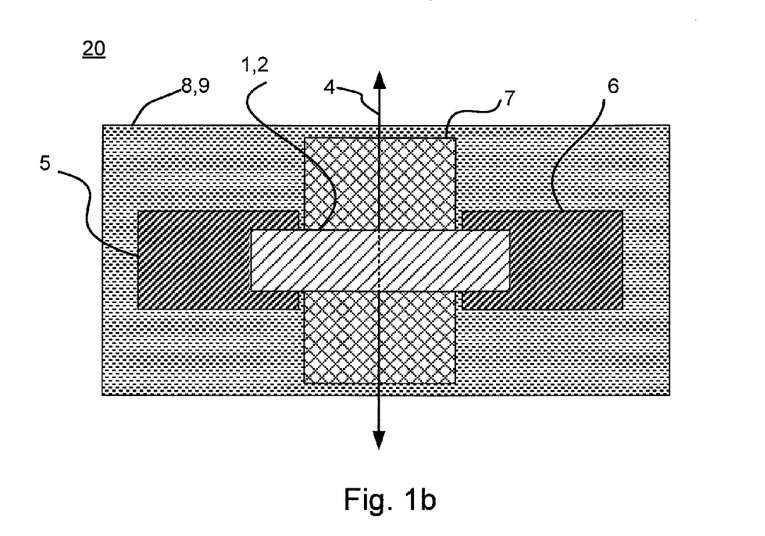

FIG. 1a schematically shows a side view of a field effect transistor 20 for chemical sensing according to a first embodiment and with schematic circuitry biasing the transistor for use as a chemical sensor 30. FIG. 1b schematically shows a bottom view of the field effect transistor 20 shown in FIG. 1a. Said figures display a design example of an air gap field effect gas sensor having a graphene layer supporting substrate 1, an electrically conducting and chemically sensitive channel 2, here formed by a continuous monocrystalline graphene layer 2a, a source electrode 5 in the form of a bonding pad, a drain electrode 6 in the form of a bonding pad, a gate electrode 7 in the form of a bonding pad, an electrically insulating gate substrate layer 8, a gate base substrate 9, and a gap 10. The chemically sensitive conducting channel 2 extends between and is electrically connected to the drain electrode 6 and the source electrode 5. The gate electrode 7 is arranged at a distance from and opposite to said chemically sensitive channel 2, so that the gap 10 is formed between the gate electrode 7 and the chemically sensitive electrically conducting channel 2. The gate electrode 7 is thus suspended above the chemically sensitive channel 2 by said gap 10 through which a chemical to be sensed can reach the chemically sensitive channel 2.

The graphene layer supporting substrate 1 may comprise any insulating or semi-insulating material that can support the graphene layer 2a and impart the electrical properties to the chemically sensitive electrically conducting channel 2 which are acceptable given the requirements of a certain application. The graphene layer substrate 1 is preferably a silicon carbide (SiC) substrate, which may affect the electronic properties of the channel 2, but not to a great enough extent that sensing is impaired and that charge neutrality cannot be achieved by application of a gate field. Although excessive charge donation is undesirable, some charge donation will typically not have a negative effect. When used in an oxygen environment, such as an air environment, a small amount of negative charge donation as from SiC may be beneficial as oxygen in the atmosphere dopes the channel and some negative charge donation from the substrate counteracts this effect.

Other possible graphene layer substrate materials include, for example, any one of $Al_2O_3$, AlN, MgO and GaN.

The continuous monocrystalline graphene layer 2a has preferably been epitaxially grown on the graphene layer supporting substrate 1, but may also have been deposited by other means onto or separately been attached to the graphene layer supporting substrate 1, for example exfoliated graphene that has been attached thereto. This may include transferring wafer scale epitaxial graphene to a substrate other than the growth substrate. The graphene layer 2a acts as the conducting channel of the field effect transistor 20. A chemical to be sensed, for example comprised in a target gas, will adsorb onto the graphene layer 2a of the chemically sensitive channel 2, thereby affecting the current flow by electron donation or withdrawal from the graphene. The graphene layer 2a preferably has a uniform thickness, and may be single, double or multi layer graphene.

Recent advances in epitaxial graphene growth on SiC has inter alia enabled high quality single layer graphene with controlled electronic properties such as carrier concentration over an entire wafer (see e.g. Yakimova et. al., "*Analysis of the Formation Conditions for Large Area Epitaxial Graphene on SiC Substrates*", Materials Science Forum, 645-648, 565-568, 2010). Due to its two-dimensionality graphene is highly influenced by the substrate, with SiC donating electrons to the graphene doping the graphene n-type and inducing a band gap (see F. Varchon, et. al. "*Structure of epitaxial graphene layers on SiC: effect of the substrate*", Phys. Rev. Lett. 99, 2007, p. 126805 and S. Y. Zhou et. al., "*Substrate-induced bandgap opening in epitaxial graphene*", Nat. Mater. 6, 2007, pp. 770-775).

The graphene layer 2a is preferably formed from graphene that has been epitaxially grown by sublimation of silicon from a silicon carbide substrate, preferably as disclosed in the pending PCT application PCT/SE2011/050328, "Process for growth of graphene", R. Yakimova, T. Iakimov, M. Syväjärvi. Wafers with such graphene may also be available from Linköping University, Sweden. Graphene produced this way can be made continuous at the wafer scale with uniform thickness and having mono layer thickness precision. This makes it particularly advantageous to use as the graphene layer 2a of the chemically sensitive conducting channel 2 and in chemical sensing applications where low detection limits are sought and/or it is desirable to be able to control and tune the chemical sensitivity properties of the chemically sensitive channel.

Still referring to FIGS. 1a-b, the source, drain and gate electrodes 5,6,7 may be in the form of bonding pads, but it is also possible with other kind of electrodes or multi-part electrodes, e.g. a respective electrode formed from a combination of a contact and a bonding pad, such as a respective source and drain contact attached to or deposited onto the graphene layer, to which corresponding bonding pads then are attached. The gate electrode 7 is preferably made of metal, including metal alloy, can be of any conventional suspended FET gate material, for example a gold or platinum electrode. Each one of the source and drain electrodes 5, 6 is also preferably made of metal, including metal alloy, and can be of any conventional suspended FET drain/source material, for example, Ti/Au or Cu/Au. The gate electrode 7 may be directly bonded to or may have additional gate contacts and gate bonding pads (not shown in figures).

In FIG. 1a, the gate electrode 7 is shown arranged, preferably deposited, for example by means of evaporation or sputtering (e.g. thermal evaporation, RF sputtering or DC sputtering), on a surface 8a of the electrically insulating gate substrate layer 8, which in turn is arranged, preferably deposited, on the gate base substrate 9. The electrically insulating gate substrate layer 8 is preferably an oxide layer, such as $SiO_2$, or any other electrically insulating material. In the shown embodiment, the electrically insulating gate substrate layer 8 and the gate base substrate 9, form together a gate substrate for the gate electrode 7. If the gate base substrate 9 is electrically insulating, the electrically insulating gate substrate layer 8 may be dispensed with and hence, in such embodiment, the gate electrode 7 may be arranged directly on the (thus electrically insulating) surface of the gate base substrate 9. The source and the drain electrode 5,6 are preferably arranged, such as deposited by means of evaporation or sputtering (e.g. thermal evaporation, RF sputtering or DC sputtering), on the same insulating surface 8a as the gate electrode 7.

The gap 10, where e.g. gases may flow through from an ambient environment, in order to adsorb on the graphene layer 2a surface, is preferably designed as a flow-throw channel as shown in the embodiment shown in FIG. 1, indicated by arrow 4 in FIG. 1b. Also other connections of the gap 10 to an ambient environment are possible. For example, there may be more than two flow-through openings to an ambient environment where the chemical to be sensed is expected. The openings need not be positioned opposite to each other. It is also possible, although typically not as advantageous, with only one opening. The gap, as shown, is preferably arranged directly adjacent to the chemically sensitive channel 2. The ambient environment can be a gaseous ambient environment, such as an air environment, or a liquid ambient environment. It is typically preferred that the gate electrode 7 and the chemically sensitive channel 2 are separated by said gap 10 only. However, as long as the electrical field in the gap is not too detrimentally affected in relation to the chemical and amount thereof to be sensed in a certain application, and the chemical in question can reach the chemically sensitive channel 2, the gap 10 may be wholly or partly occupied by some material.

In the embodiment shown in FIG. 1, the length of the graphene layer 2a of the chemically sensitive channel 2, that is, the distance between the source and drain electrodes 5,6 connecting to it, is greater than its lateral width. Such relation is preferred since it confines the electrons in the conducting channel in two dimensions which may enable further control over the electrical properties e.g. band gap of the graphene channel; however, it is also possible with a width that is greater than the length. The length and width may be about the same order of size. In one embodiment for evaluation purposes, the length was about 5 mm and the width about 2 mm. However, the sizes may be magnitudes smaller than this. Typically the sizes are in the domain of millimeters or micrometers. Lower limits may be determined by ease of production of the device. The height of the gap 10, that is, the distance between the gate electrode 7 and the chemically sensitive channel 2, is preferably below about 1 µm. A lower limit may be determined by diffusion speeds of chemicals to be sensed into the gap.

When the field effect transistor is being used for chemical sensing, such as when being part of a chemical sensor, the chemical sensor is typically configured to electrically bias the field effect transistor so that a chemical to be sensed which comes in contact with the chemically sensitive channel results in a change of an electrical signal, wherein the change is indicative of the chemical being sensed. As should be recognized by the skilled person, a field effect transistor for gas sensing may be biased and controlled in different ways, which may provide different chemical indicative signals. With reference to the embodiment of FIG. 1, changing a voltage applied to the gate electrode 7 will affect the current flow through the electrically conducting and chemically sensitive channel 2 and the electronic properties of the graphene layer 2a can be modulated by the voltage. A chemical adsorbing onto the graphene from the air gap 20, may donate or withdraw electrons from the graphene channel and may also affect the mobility in the graphene channel, causing a change in the resistance of the graphene channel.

FIG. 1a schematically shows an embodiment of a chemical sensor 30 comprising the field effect transistor 20 connected to exemplary circuitry. A current source 22 is connected to and between source and drain electrodes 5,6 and arranged to apply a constant current. A voltage source 21 of the sensor 30 is connected to the gate electrode 7 and is arranged to set a gate voltage that preferably gives a maximum change in graphene resistance in a range of gas concentration sensing is required in. A chemical adsorbing onto the graphene can then be sensed by measuring a change in voltage between source and drain required to maintain the constant current.

In another embodiment, a voltage source may be arranged to apply a constant voltage between source and drain electrodes 5,6 and an ampere meter may be arranged to measure current between the source and drain electrodes 5,6. Another voltage source may be connected to the gate electrode 7 and be arranged to set a gate voltage to maintain constant current between source and drain electrodes 5,6. A chemical adsorbing onto the graphene can then be sensed by monitoring change in the applied gate potential required to keep the current constant. Another option is to apply a constant gate voltage and use the ampere meter to detect any change in the current flow, the change in current thus becoming indicative of the sensed chemical.

Regardless what exact signal is indicative of the sensed chemical in a sensor using the field effect transistor for chemical sensing, the signal can be used to e.g. calculate the concentration of the chemical adsorbed on the channel, which in turn is a measure of the concentration of the chemical in e.g an ambient gas or liquid environment.

Figure 2A:
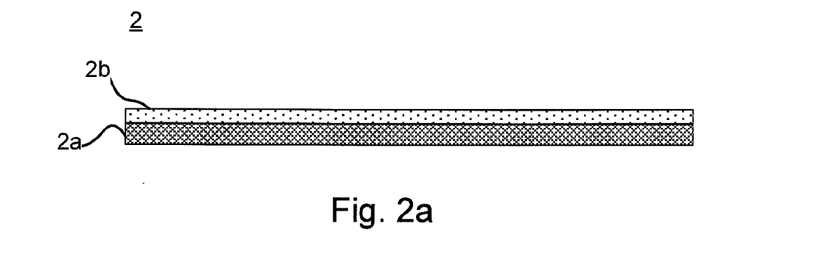
FIG. 2a schematically shows a side view of a field effect transistor chemical sensitive channel with an exemplary first type of surface treatment.
Figure 2B:
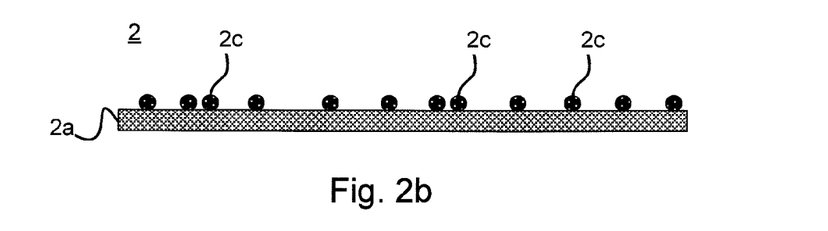
FIG. 2b schematically shows a side view of a field effect transistor chemical sensitive channel with an exemplary second type of surface treatment.

When the field effect transistor, such as the field effect transistor 20 shown in FIG. 1, is used for chemical sensing, this typically involves some guiding to the gap 10 from the ambient environment where a chemical to be sensed is expected. As the skilled person realizes, this can be accomplished in a number of different ways, e.g. as in conventional sensors. In a simple variant the openings of the flow-through channel discussed above may directly connect to the ambient environment, but typically there is at least some pre-filtering involved so that pollution, dirt other undesirables or large particles are not allowed to clog the gap or cause other damage, which e.g. may reduce the life time of the sensor. In the embodiment shown in FIG. 1, the chemically sensitive channel 2 is formed of the graphene layer 2a only. However, the graphene layer 2a may be surface treated for chemical selectivity so that only selected types of chemicals are detected by the graphene layer 2a and/or so that certain types of chemicals are prevented from reaching the graphene layer 2a. The chemically sensitive channel may e.g. be pure graphene, surface doped graphene or surface modified graphene to enhance the sensitivity towards some gases that are not usually detectable or improve selectivity towards one gas species or set of gas species over another. The gas sensitive channel may be modified to introduce selectivity to different gases by deposition of metal nanoparticles and/or polymers. FIG. 2a schematically shows a side view of a chemically sensitive channel 2 that has been surface treated by a polymer forming a polymer coating 2b on the graphene layer 2a. FIG. 2b schematically shows a side view of a chemically sensitive channel 2 that has been surface treated by metal nanoparticles 2c. The deposition of metal nanoparticles and polymers onto carbon based sensors is a developed field. For example, in the article "*Gas Sensor Array Based on Metal-Decorated Carbon Nanotubes*", Star et. al, *Journal of Chemical Physics B* 2006, 110(42), pp 21014-21020, deposition of metal particles by evaporation and electrochemical deposition are compared, and other methods are reviewed. Also, in the article "*Toward Large Arrays of Multiplex Functionalized Carbon Nanotube Sensors for Highly Sensitive and Selective Molecular Detection*", Qi et. al, *Nano Letters* 2003 vol. 3, no. 3, 347-351, increased selectivity with polymer coatings polyethyleneimine (PEI) and nafion is described. The devices were coated by immersion of PEI in a methanol solution followed by baking. The nafion coating was achieved through drying of a 1% nafion in water solution over the sensor surface. Hence, a chemically selective coating may be applied to the graphene layer 2a to enhance selectivity between gases. The graphene layer 2a may also be modified with catalytic metals or polymers to introduce sensitivity to gases that are not electrically donating or withdrawing or to enhance the adsorption of non-adsorbing gases or to increase the sensitivity towards one gas over another. The aforementioned enhancements may also be accomplished by substitutional or edge doping of the graphene layer 2a which may also improve stability of the device.

Referring again to the embodiment of FIG. 1, the presented device may comprise two separate parts mounted together: the chemically sensitive channel 2 supported by the graphene layer substrate 1 as a first part 11 and the gate electrode 7 arranged on an insulating surface 8a of the gate substrate 8,9 as a second part 12. Also the drain electrode 6 and the source electrode 5 arranged on the insulating surface 8a of the gate substrate 8,9 preferably belong to the second part 12. The mounting brings the drain electrode 6 and the source electrode 5 in physical contact with the first part 11, thereby establishing electrical connection between the graphene layer 2a and the source electrode 5 and the drain electrode 6. Attachment between the first and second part may e.g. involve flip chip bonding, adhesive technology or clamping. The first and second parts can thus be produced separately, and device preparation and processing steps involving presence of the graphene layer can be minimal so as to avoid damage to the graphene layer. The size of the source and drain electrodes can be used to control the size, in particular the height of the gap 10.

In one embodiment source and drain contacts may be deposited onto the graphene layer 2a and thus belong to the first part, with the contact to source and drain bonding pads, belonging to the second part, being made with, for example, flip chip bonding or adhesive technology. In another embodiment source and drain contacts may be deposited atop the source drain bonding pads of the second part and the graphene channel and graphene layer substrate 1 may be held in place by clamping.

Figure 3:
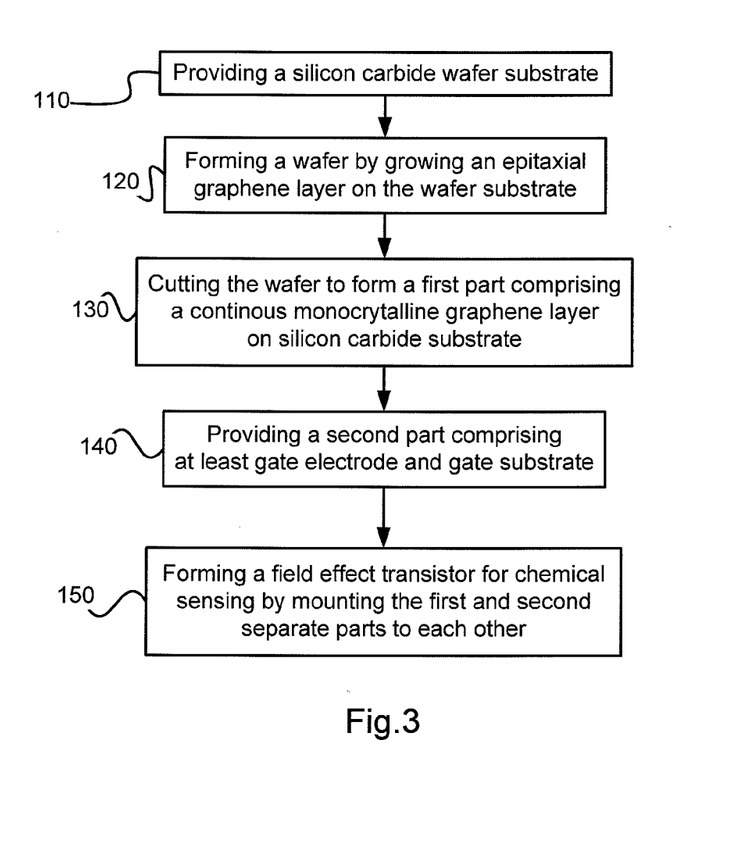
FIG. 3 is a block diagram schematically showing steps in a method for providing a field effect transistor for chemical sensing.

FIG. 3 is a block diagram schematically showing steps in a method for producing a field effect transistor for chemical sensing, for example the field effect transistor 20 shown in FIG. 1. In a first step 110 a silicon carbide wafer substrate is provided, then, in a step 120, a wafer is formed by growing an epitaxial graphene layer on the wafer substrate, preferably by sublimation of silicon from the silicon carbide substrate. The first and second steps are preferably performed in accordance with the above mentioned pending PCT application PCT/SE2011/050328. Thereafter, in a step 130, the wafer is cut so that a continuous monocrystalline graphene layer arranged on a graphene layer substrate is formed from a cut piece of the epitaxial graphene layer with its underlying part of the silicon carbide wafer substrate. The cut piece may form a first part, such as the first part 11 in FIG. 1a and as discussed above. In another embodiment the grown epitaxial graphene layer is removed from the substrate of growth and transferred to another wafer substrate to form a wafer that subsequently is cut. In a step 140, a second part, such as the second part 12 in FIG. 1a and as discussed above, is provided separately and comprising at least the gate electrode arranged on an insulating surface of a gate substrate. Preferably the second part also comprises a drain electrode and a source electrode arranged on the insulating surface of the gate substrate. In a step 150, a field effect transistor, such as the field effect transistor 20 in FIG. 1 and as discussed above, is formed by mounting the first and second separate parts to each other. By the mounting, the first and second parts are preferably physically connected by the source and drain electrodes and attachment between the first and second part may e.g. involve flip chip bonding, adhesive technology or clamping.

Any illustration and description in the drawings and in the foregoing description are to be considered exemplary and not restrictive. The invention is not limited to the disclosed embodiments.

The present invention is defined by the claims and variations to the disclosed embodiments can be understood and effected by the person skilled in the art in practicing the claimed invention, for example by studying the drawings, the disclosure, and the claims. Use of the word "comprising" in the claims does not exclude other elements or steps, and use of the article "a" or "an" does not exclude a plurality. Occurrence of features in different dependent claims does not per se exclude a combination of these features. Any method claim is not to be construed as limited merely because of the presentational order of the steps. Any possible combination between independent steps of any method claim shall be construed as being within scope, although the independent steps, by necessity, must occur in some order. Any reference signs in the claims are for increased intelligibility and shall not be construed as limiting the scope of the claims.

The invention claimed is:

1. A field effect transistor for chemical sensing, comprising
   a drain electrode,
   a source electrode,
   an electrically insulating graphene layer substrate,
   a continuous monocrystalline graphene layer arranged on said graphene layer substrate, the monocrystalline graphene layer at least partially defining an electrically conducting and chemically sensitive channel, said monocrystalline graphene layer and said chemically sensitive channel extending between and being electrically connected to said drain electrode and source electrode, and
   a gate electrode being arranged at a distance from and opposite to said chemically sensitive conducting channel so that the gate electrode and the monocrystalline graphene layer together with the drain and source electrodes define a gap in which the gate electrode and chemically sensitive conducting channel face one another on opposite sides of the gap in a first direction, and in which the drain and source electrodes face one another on opposite sides of the gap in a second direction perpendicular to the first direction, and through which a chemical to be sensed is introducible to reach the chemically sensitive channel within the gap,
   wherein the gate electrode is arranged on an electrically insulating surface of a gate substrate, and the chemically sensitive channel and the graphene layer substrate are spaced apart from the gate substrate by the drain and source electrodes, and wherein the chemically sensitive channel and the graphene layer substrate belong to a first separate part that is mounted to a second separate part comprising at least the gate electrode.

2. The field effect transistor as claimed in claim 1, wherein the graphene layer has uniform thickness, preferably a predetermined thickness of one or more monolayers of graphene.

3. The field effect transistor as claimed in claim 1, wherein the graphene layer is an epitaxial layer.

4. The field effect transistor as claimed in claim 3, wherein the graphene layer substrate is the substrate on which the graphene layer was epitaxially grown.

5. The field effect transistor as claimed in claim 1, wherein the graphene layer substrate is a silicon carbide substrate.

6. The field effect transistor as claimed in claim 5, wherein the graphene layer was epitaxially grown on the silicon carbide substrate by sublimation of silicon from the silicon carbide substrate.

7. The field effect transistor as claimed in claim 1, wherein the graphene layer has been surface treated for chemical selectivity so that only selected types of chemicals are detected by the graphene layer so that certain types of chemicals are prevented from reaching the chemically sensitive channel.

8. The field effect transistor as claimed in claim 7, wherein the surface treatment comprises deposition of metal particles and/or polymers.

9. The field effect transistor as claimed in claim 1, wherein the gap is arranged directly adjacent to the chemically sensitive channel and is in connection with an ambient environment so that the chemical to be sensed can reach the gap from the ambient environment, wherein said ambient environment is a gaseous ambient environment, such as an air environment, or a liquid ambient environment.

10. The field effect transistor as claimed in claim 1, wherein the gate electrode and the chemically sensitive channel are separated by said gap only.

11. The field effect transistor as claimed in claim 1, wherein the gate electrode is made of metal, such as of gold or platinum.

12. The field effect transistor as claimed in claim 1, wherein the gap is designed as a flow-through channel, the height of which is defined by the distance between the gate electrode and the chemically sensitive channel.

13. The field effect transistor as claimed in claim 12, wherein the second part further comprises the drain electrode and the source electrode arranged on the insulating surface of the gate substrate, and which by the mounting are brought in physical contact with the first part, thereby establishing the electrical connection between the graphene layer and the source electrode and the drain electrode.

14. The field effect transistor as claimed in claim 12, wherein said flow-through channel has a closed cross-section.

15. A chemical sensor comprising the field effect transistor as claimed in claim 1, wherein the chemical sensor comprises circuitry arranged to electrically bias the field effect transistor so that a chemical to be sensed which comes in contact with the chemically sensitive channel results in a change of an electrical signal, wherein the change is indicative of the chemical being sensed.

16. The chemical sensor as claimed in claim 15, wherein the circuitry comprises a current source arranged to flow a constant current between the source electrode and the drain electrode and by comprising a voltage source arranged to supply a constant voltage to the gate electrode, wherein the electrical signal indicative of the sensed chemical is a voltage between the source electrode and the drain electrode.

17. The chemical sensor as claimed in claim 15, wherein the circuitry comprises a voltage source arranged to apply a constant voltage between the source electrode and the drain electrode, wherein the electrical signal indicative of the sensed chemical is a gate electrode voltage required to maintain a constant current between the source electrode and the drain electrode.

18. Use of a field effect transistor as claimed in claim 1, for chemical sensing.

19. The use as claimed in claim 18, wherein the chemical sensing comprises guiding a chemical to be sensed from an ambient environment to the gap.

20. A method for producing the field effect transistor as claimed in claim 1, wherein the method comprises the steps of:
   providing a wafer that comprises an epitaxial graphene layer on a silicon carbide wafer substrate; and
   forming the continuous monocrystalline graphene layer of the field effect transistor from the epitaxial graphene layer;
   providing the continuous monocrystalline graphene layer arranged on the graphene layer substrate as a first separate part;
   providing a second separate part comprising the gate electrode arranged on an insulating surface of a gate substrate; and
   forming the field effect transistor for chemical sensing by mounting the first and second separate parts to each other.

21. The method as claimed in claim 20, wherein the step of providing the wafer comprises:
   providing a silicon carbide wafer substrate; and
   growing the epitaxial graphene layer on the silicon carbide wafer substrate by sublimation of silicon from the silicon carbide wafer substrate.

22. The method as claimed in claim 20, wherein the step of forming the continuous monocrystalline graphene layer comprises:
   cutting the wafer so that the continuous monocrystalline graphene layer arranged on the graphene layer insulating substrate is formed from a cut piece of the epitaxial graphene layer with underlying part of the silicon carbide wafer substrate.

23. The method as claimed in claim 20, wherein the second separate part also comprises the drain electrode and the source electrode arranged on the insulating surface of the gate substrate.

\* \* \* \* \*